US009126035B2

(12) United States Patent
Valoir

(10) Patent No.: US 9,126,035 B2
(45) Date of Patent: Sep. 8, 2015

(54) SHAPED CONFORMING MEDICAL BALLOONS

(75) Inventor: Tamsen Valoir, Houston, TX (US)

(73) Assignee: RadiaDyne LLC, Houston, TX (US)

( * ) Notice: Subject to any disclaimer, the term of this patent is extended or adjusted under 35 U.S.C. 154(b) by 318 days.

(21) Appl. No.: 13/591,546

(22) Filed: Aug. 22, 2012

(65) Prior Publication Data

US 2013/0109906 A1    May 2, 2013

Related U.S. Application Data

(60) Provisional application No. 61/551,745, filed on Oct. 26, 2011.

(51) Int. Cl.
*A61N 5/10* (2006.01)
*A61M 25/10* (2013.01)
*A61B 19/00* (2006.01)
*A61B 17/00* (2006.01)

(52) U.S. Cl.
CPC ......... *A61N 5/1014* (2013.01); *A61M 25/1002* (2013.01); *A61N 5/1049* (2013.01); *A61N 5/1071* (2013.01); *A61B 19/40* (2013.01); *A61B 2017/00079* (2013.01); *A61B 2017/00084* (2013.01); *A61B 2019/207* (2013.01); *A61B 2019/5466* (2013.01); *A61N 2005/1094* (2013.01); *A61N 2005/1097* (2013.01)

(58) Field of Classification Search
CPC .................... A61B 19/40; A61B 2017/00079; A61B 2017/00084; A61B 2019/207; A61B 2019/5466; A61N 5/1014; A61N 5/1071; A61N 2005/1094; A61N 5/1049; A61M 25/1002; A61M 5/1004

USPC .............. 604/103.03, 103.07, 916, 103.06, 604/103.08, 96.01, 99.01, 99.02, 100.01, 604/100.02, 103.05, 104, 164.1, 509; 606/190, 191, 192, 197, 194, 193, 196, 606/198, 199; 623/1.11

See application file for complete search history.

(56) References Cited

U.S. PATENT DOCUMENTS

| | | | | | |
|---|---|---|---|---|---|
| 1,690,995 | A | * | 11/1928 | Pratt | 606/192 |
| 4,018,231 | A | * | 4/1977 | Wallace | 128/207.15 |
| 4,509,514 | A | * | 4/1985 | Brain | 128/207.15 |
| 4,932,956 | A | * | 6/1990 | Reddy et al. | 606/192 |
| 4,983,167 | A | * | 1/1991 | Sahota | 606/194 |
| 5,007,437 | A | * | 4/1991 | Sterzer | 607/138 |
| 5,049,131 | A | * | 9/1991 | Deuss | 604/98.01 |
| 5,108,370 | A | * | 4/1992 | Walinsky | 604/102.02 |
| 5,232,446 | A | * | 8/1993 | Arney | 604/103.07 |
| 5,348,010 | A | * | 9/1994 | Schnall et al. | 600/422 |
| 5,451,232 | A | * | 9/1995 | Rhinehart et al. | 606/192 |
| 5,476,095 | A | * | 12/1995 | Schnall et al. | 600/423 |
| 5,501,667 | A | * | 3/1996 | Verduin, Jr. | 604/101.01 |
| 5,562,606 | A | * | 10/1996 | Huybregts | 604/8 |
| 5,575,771 | A | * | 11/1996 | Walinsky | 604/96.01 |
| 5,607,443 | A | * | 3/1997 | Kieturakis et al. | 606/192 |

(Continued)

OTHER PUBLICATIONS

Polyurethane Properties, Oct. 12, 2010, American Urethane, Inc.*

*Primary Examiner* — Ryan Severson
*Assistant Examiner* — Christian Knauss
(74) *Attorney, Agent, or Firm* — Boulware & Valoir

(57) ABSTRACT

A shaped medical balloon is provided that has a conforming shape, yet is inexpensive to manufacture, wherein a central portion of the balloon is folded inside and welded together at the fold and is further welded to said lumen, thus creating a conforming depression in the surface of said balloon at the central portion.

13 Claims, 5 Drawing Sheets

(56) References Cited

U.S. PATENT DOCUMENTS

| | | | |
|---|---|---|---|
| 5,653,683 A * | 8/1997 | D'Andrea | 604/21 |
| 5,720,717 A * | 2/1998 | D'Andrea | 604/21 |
| 5,772,680 A * | 6/1998 | Kieturakis et al. | 606/190 |
| 5,817,123 A * | 10/1998 | Kieturakis et al. | 606/192 |
| 5,865,801 A * | 2/1999 | Houser | 604/103.07 |
| 6,007,517 A * | 12/1999 | Anderson | 604/103.04 |
| 6,251,059 B1 * | 6/2001 | Apple et al. | 600/3 |
| 6,565,589 B1 * | 5/2003 | Jervis et al. | 606/190 |
| 6,796,972 B1 * | 9/2004 | Sinofsky et al. | 604/264 |
| 6,893,456 B2 * | 5/2005 | Lumauig | 623/1.11 |
| 7,041,079 B2 * | 5/2006 | Yozu et al. | 604/96.01 |
| 7,220,252 B2 * | 5/2007 | Shah | 604/500 |
| 7,976,497 B2 * | 7/2011 | Shah et al. | 604/103.06 |
| 8,080,031 B2 | 12/2011 | Isham | |
| 8,257,314 B2 * | 9/2012 | Agnew | 604/164.13 |
| 2003/0028097 A1 * | 2/2003 | D'Amico et al. | 600/427 |
| 2003/0028211 A1 * | 2/2003 | Crocker et al. | 606/192 |
| 2003/0114878 A1 * | 6/2003 | Diederich et al. | 606/192 |
| 2004/0236209 A1 * | 11/2004 | Misic et al. | 600/423 |
| 2006/0224034 A1 * | 10/2006 | Reever | 600/3 |
| 2007/0112306 A1 * | 5/2007 | Agnew | 604/164.13 |
| 2007/0239110 A1 * | 10/2007 | Shah | 604/96.01 |
| 2008/0183202 A1 | 7/2008 | Isham | |
| 2008/0300619 A1 * | 12/2008 | Isham | 606/197 |
| 2009/0043151 A1 * | 2/2009 | Gobel | 600/31 |
| 2009/0221899 A1 * | 9/2009 | Isham | 600/407 |
| 2009/0247945 A1 * | 10/2009 | Levit et al. | 604/103 |
| 2010/0145379 A1 * | 6/2010 | Isham | 606/192 |
| 2010/0152654 A1 * | 6/2010 | Tilson et al. | 604/103.06 |
| 2010/0179582 A1 * | 7/2010 | Isham et al. | 606/192 |
| 2011/0098683 A1 * | 4/2011 | Wiita et al. | 604/544 |

* cited by examiner

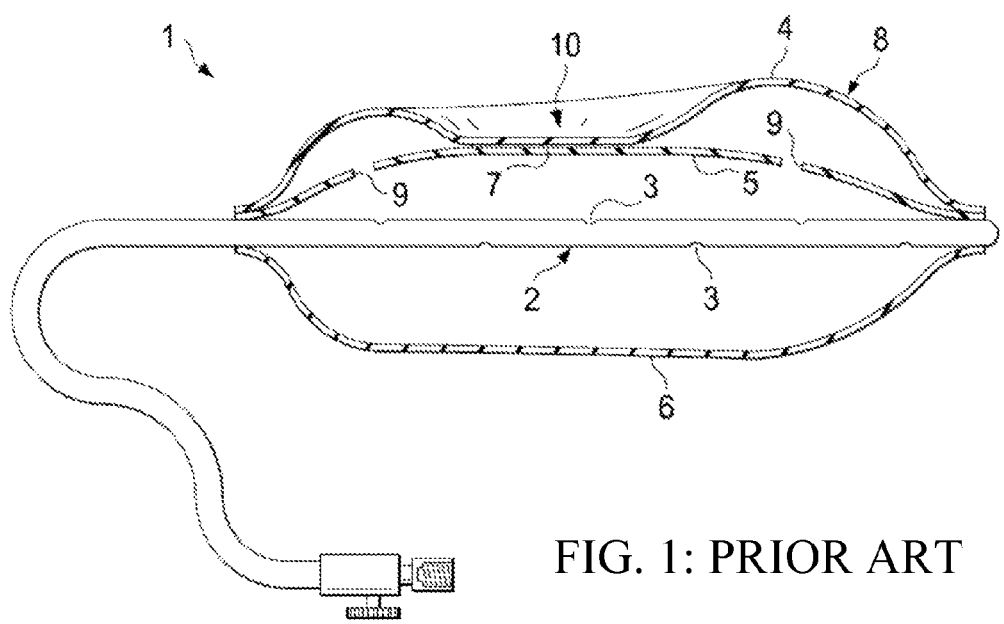
FIG. 1: PRIOR ART
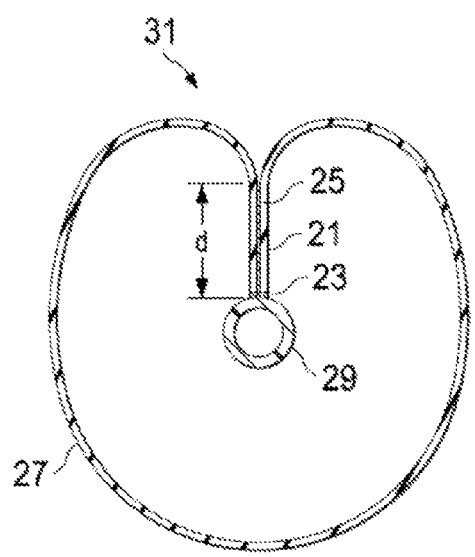
FIG. 2
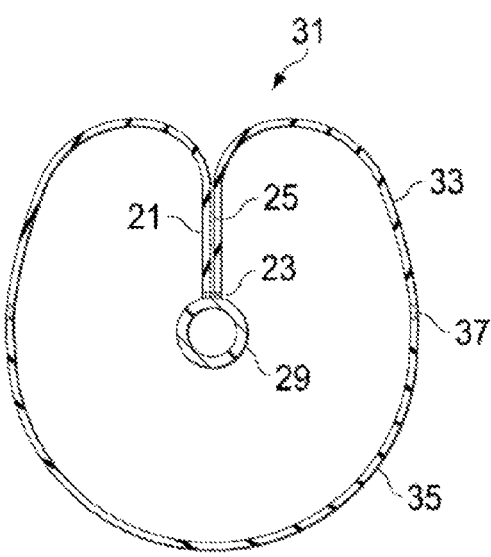
FIG. 3

SHAPED CONFORMING MEDICAL BALLOONS

PRIOR RELATED APPLICATIONS

This application claims priority to Ser. No. 61/551,745, filed Oct. 26, 2011, and incorporated by reference in its entirety.

FEDERALLY SPONSORED RESEARCH STATEMENT

Not applicable.

JOINT RESEARCH AGREEMENT

Not applicable.

FIELD OF THE INVENTION

The invention relates to shaped medical balloons that retain their shape, even on hyperinflation or squeezing, as well as methods of making and uses for same.

BACKGROUND OF THE INVENTION

Prostate cancer is a form of cancer that develops in the prostate, a gland in the male reproductive system. Most prostate cancers are slow growing; however, there are cases of aggressive prostate cancers. The cancer cells may metastasize (spread) from the prostate to other parts of the body, particularly the bones and lymph nodes. Prostate cancer may cause pain, difficulty in urinating, problems during sexual intercourse, or erectile dysfunction. Other symptoms can potentially develop during later stages of the disease.

Treatment options for prostate cancer with intent to cure are primarily surgery, radiation therapy, stereotactic radiosurgery, and proton therapy. Other treatments, such as hormonal therapy, chemotherapy, cryosurgery, and high intensity focused ultrasound (HIFU) also exist, although not FDA approved, depending on the clinical scenario and desired outcome.

Radiation therapy has some advantages over surgery: the patient can continue to work during treatment, and does not have as long a recovery period as would occur after surgery. In addition, radiation therapy can cure localized prostate cancer, as can surgery. Prostate cancer is treated with both external and internal radiation therapy, and some men will be treated with both types. Internal radiation therapy, also known as brachytherapy, is a procedure in which radioactive seeds are implanted directly into the prostate to kill the cancer. External radiation therapy typically is given five days a week for a period of six to eight weeks, using a machine that looks much like a regular X-ray machine. The procedure is not painful, and each treatment lasts only a few minutes.

In external beam therapy, several beams are aimed at the tumor, and radiation is thus concentrated at the intersection point of the various beams. This therapy is often combined with the use of flexible balloons, or more rigid objects, to hold healthy tissue away from the target area, thus minimizing the dose to healthy tissue. For example, a rectal balloon can be used to push the rectal wall away from the prostate.

The side effects of external beam radiation therapy tend to be less severe than the side effects of other prostate cancer treatments. However, there is still the possibility of incontinence, erectile dysfunction, rectal damage and the like. One of the important contributors to these side effects is uncertain positioning in daily set-up and as caused by tumor motion. Such uncertainties can be caused by internal movements (for example, respiration, bladder filling, peristaltic motions of the gastrointestinal tract, rectal gas and the like) and movement of external skin marks relative to the tumor position.

In fact, researchers report the intrinsic motion of the prostate gland can be as much as 5 mm in the anterior to posterior direction due to rectal peristalsis. This has led to an additional 3 to 5 mm margin being added to the radiation field to account for prostate motion, along with 2 to 5 mm for setup error and dose buildup each, for a total margin of 10 to 15 mm to allow for the dose to reach 100% of the prescribed dose. If internal prostate motion is not addressed, it can lead to under-dosing of the target, and/or over-dosing of healthy surrounding tissues.

External patient positioning systems attempt to minimize anatomical variations by providing a secure and reproducible scaffolding, allowing the patient to comfortably maintain a relatively stable external position. However, external positioning systems cannot compensate for daily internal anatomical variations and organ movement due to breathing, rectal peristalsis, and rectal gas, which have been shown to be the major component of variation in target localization.

One way of minimizing the effects of such internal motions is to compress the tissue with an inflatable balloon. However, most of the balloons on the market are nonconforming, thus lose their shape when overinflated or squeezed. Thus, these balloons are less than an ideal solution, the prostate easily sliding off one side of the balloon or the other when in use.

RadiaDyne has provided an innovative solution to this problem, marketing a conforming rectal balloon that holds its shape even in the highly mobile environment of the rectum. This revolutionary new design has allowed the company to capture more than 90% of the prostate immobilizing rectal balloon market.

In more detail, the conforming immobilizing balloon of Ser. No. 11/966,544 et seq (all incorporated by reference herein) consists of three layers of material welded together at the edges, wherein the middle layer functions as a baffle and is also welded or glued to the upper layer. This weld or attachment point between the inner and upper layers provides a physical constraint against expansion on inflation or compression, and thus provides a groove or depression into which the prostate can be wedged during treatment.

Application Ser. No. 12/034,470 (incorporated by reference) provided a further improvement, allowing the distal surface to bulge on additional inflation, thus further wedging the seminal vesicles into position, and holding the balloon against expulsive forces. The distal bulge can be achieved in any number of ways, including making that portion of thinner material, making that portion of more elastomeric material. But, more simply, the distal bulge can be made by shifting the groove weld proximally, thus the greater amount of elastomeric material on the distal side will naturally stretch more. It is also possible to make a bulge or protrusion by welding on additional material, e.g., semicircular portion of material (like the finger on a glove), or by pre-shaping the balloon, such as by pressure/vacuum forming.

Both of these balloons were significant improvements over the prior art of non-conforming balloons, which were generally elastomeric and not physically constrained against bulging on compression, such that the prostate could easily slide away. The RadiaDyne conforming balloons allowed reduction of margins, reduction of dose to the rectum, reduction in margin surrounding the prostate, displacement of low lying bowel, reduction of dose related side effects, and the ability to escalate dose and increase the rate of local tumor control of prostate cancer. However, these balloons are also expensive to manufacture, each weld contributing to complexity and cost.

What is needed in the art are further improvements in balloon design that allow the manufacture of a shaped balloon, but is less expensive than the trilayer RadiaDyne balloons described above, yet is still a conforming balloon having a suitable shape.

SUMMARY OF THE INVENTION

Generally speaking, the invention is less expensive, shaped medical balloon of a unitary or bilayer construction that is still conforming in a highly mobile environment. Such balloon is made by molding a balloon shape in the traditional way (e.g., by dipping a mold into a latex or other polymer solution) to obtain a balloon of unitary construction or by welding two films together at the edges.

The balloon is then welded to itself or the lumen (or both) to make the desired conforming depression. There are several ways of achieving this. In one method, the balloon is pinched or folded at a generally central area where a conforming depression is needed, and the pinched surface portions glued or otherwise welded together, such that the pinch portion is inside the balloon rather than on an exterior side. In preferred embodiments, the pinch is also welded to a central lumen, providing a further restraint against expansion.

In an alternative embodiment, the pinch is omitted, and the upper layer simply welded to a central lumen. In such embodiment, it may be necessary to use a somewhat less flexible lumen, so that forces do not pull the lumen too far out of its central, generally straight alignment. As yet another alternative, however, both upper and lower layers can be welded to the lumen at the groove, thus balancing opposing forces.

In yet another embodiment, a baffle can be used to provide some distance between the surface of the balloon and the lumen, thus allowing close control over the depth of the depression. However, baffle construction is not preferred as requiring more material and more welds.

In yet other embodiments, where both sides of the balloon need depressions, the upper surface can be welded to the lower surface, instead of the lumen, either directly or indirectly via baffle.

The balloon with the conforming depression is also welded to the lumen at least at the proximal end, and preferably at both ends, the lumen fitted with standard valve means, and the balloon sterilized (if needed) and packaged for sale.

By "weld" herein, we mean any method of attaching two layers of polymeric film together. Thus, the welds or attachment points can be glued, heat welded, RF welded, ultrasound welded, solvent welded, hot gas welded, freehand welded, speed tip welded, extrusion welded, contact welded, hot plate welded, high frequency welded, injection welded, friction welded, spin welded, laser welded, impulse welded or any other means known in the art.

By "central" portions welded together herein, we are distinguishing from edge welds in a bilayer construction. Thus, central refers to portions inside the edge welds, but an exactly central position is not implied.

By "pinch" what is meant is that a balloon surface is folded at a small area, creating a portion where the balloon is bilayered. In other words, the surface is bent and the two surfaces on either side of the bend brought together so as to be juxtaposed or directly adjacent. This pinch can be glued or otherwise welded, making the bilayer structure permanent. Outside of the pinch area, the balloon has the usual single layer structure.

By "fold inside" or "pinch inside" or "folded internally" or any similar phrases, what is meant is that the material is folded such that the outer surfaces of the balloon are in juxtaposition, and so that the bilayer portion is "inside" the balloon.

By "conforming" depression what is meant is that the depression is retained even on hyperinflation or squeezing of the balloon.

By "baffle" what is a meant is a small strip of material of length less than the expanded width between the two surfaces to which it is welded. The baffle is thus welded to one or more surfaces of the balloon and/or the lumen, and serves to control the depth of a conforming depression, longer baffles leading to shallower depressions, shorter baffles leading to deeper depressions.

The pinch described above, serves the same function as the baffle, but is not a separate piece of material, but made directly from the balloon surface material.

By "groove" what is meant is a depression that is longer than its width.

By "dimple" what is meant is a depression that is about as long as its width.

For rectal purposes the balloon is generally ovoid in shape, but pointed at each end like a football for easier insertion. However, other shapes may be desired for other purposes. A single groove positioned centrally, but proximally shifted, may be ideal for prostate use, since this provides a longitudinal groove into which the prostate can be wedged as well as a distal bulge to stabilize the seminal vesicles.

The balloon is of course fitted with means for introducing air or other fluid such as water or contrast, and keeping the fluid therein, and these can be of any shape or design known in the art. Typical means for introducing fluids is a lumen or flexible tube with stopcock or other valve means and connector for fluidly connecting to a syringe or other air or fluid source. Alternatively, a luer lock can be used in place of a stopcock and connector.

Different shape and/or length of outer surfaces are possible and cylinders, bulges, flares, and indentations can be provided as needed for the body cavity in question.

When the balloon is intended for rectal use, it can also be advantageously provided with a gas lumen that travels the complete length of the balloon, protruding from the distal end and having openings past the distal end of the balloon, thus providing a passageway for the escape of gas. Ideally, such lumen has a smooth, rounded, soft tip with multiple holes for gas entry, and is positioned centrally inside the balloon, although other positions and shapes are possible. In such cases, the fluid entry lumen for inflating the balloon need not traverse the length of the balloon, but only enter the balloon at the proximal end via, e.g., a low profile inlet fitment. Nested lumens, two lumens welded together, and bifurcated lumens can also be used, so long as there is fluid connection to the inside of the balloon, and a second fluid passageway traversing the balloon, but not in fluid connection with the balloon interior, such that gas can escape therethrough.

The shaped medical balloon can also comprise radio-opaque markers that can be used in imaging for accurate placement of the balloon, and could also comprise passive radiation sensors, such as is used in radiation badges, plastic scintillating detectors or MOSFET sensor. Opaque markers can be letters indicating top (T) or right (R) and left (L) sides of the balloon, or numbers or any other shape, and can be particularly advantageous for those balloons whose shape is not radially symmetrical. An end marker can also be placed on the very tip of a gas lumen, if included therein (see e.g., 64 in FIG. 5B). Electronic or active radiation sensors can also be used, but will contribute significantly to expense, and may be less appropriate for a disposable balloon.

Other sensors, such as electromagnetic motion sensors, temperature sensors, pressure sensors oxygen sensors, pH sensors, and the like can be added. Numerical indicia on a lumen or shaft can also be provided to mark insertion depth.

The balloon is preferably made of thermoplastic elastomers (TPE), especially thermoplastic polyurethane. Other balloon fabrication materials include latex, polyethylene (PE), polypropylene (PP), silicone, vinyl, polyvinyl chloride (PVC), low density polyethylene (LDPE), polyvinylidene chloride (PVDC), linear low density polyethylene (LLDPE), polyisobutene (PIB), and poly[ethylene-vinylacetate] (EVA) copolymers, nitrile, neoprene, and the like. It is also possible to use a laminar plastic, having more than one layer, e.g., a tougher interior layer and a biocompatible or slippery outer layer.

The ideal material is a translucent, biocompatible material, that has a durometer of less than 80-100 Shore A (ASTM D2240 or ISO 868), a tensile strength of at least 3000 psi (ISO 527-3 or ASTM D882-02), a 100% modulus of 500-1000 psi (ASTM D412), an elongation at break of at least 300% (ASTM D412), and that is air tight even under 150% stretch. In some applications, the material should also be sterilizable, without loss of its qualities such as strength, etc.

In some embodiments, the shaped medical rectal balloon is provided with locking stopper that serves to prevent the balloon from sliding further into the body cavity, such as the rectum, which it may be prone to do without such stopper. The stopper has an upper portion, generally smoothly rounded or semispherical, which fits snugly against the anus, and a hole, through which the lumen(s) is/are threaded. Other shapes may be used for other body cavities, and the stopper may be optional for other cavities.

A lower locking portion of the stopper snap locks against the lumen without blocking fluid entry, and preferably has interior fins or ridges lining its hole that engage the lumen, and prevent sliding, as a locking mechanism without such ridges is prone to do. Another means of making a locking stopper is to line the interior of the hole through which the lumens are threaded with a tacky material, so that friction locks the stopper in place. Another method is to make a portion of the interior compress the lumen enough to lock it in place, but not so much as to block the lumen. A conical interior may be beneficial for this. A hinge on the locking portion allows the lock to be opened, and the lock snap fits shut.

The details of the locking mechanism can be as shown in US20100145379, incorporated herein by reference. The upper portion of the locking stopper of US20100145379 has a groove reaching to the central hole, so that the stopper need not be threaded over the lumen, but this groove can be eliminated and thus prevent stopper loss once the valves and luer lock are added to the end of the lumen. Of course, the central hole is not necessarily round as shown in US20100145379, especially if two are welded together, but should reflect the cross section of the lumen(s).

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", and "include" (and their variants) are open-ended linking verbs and allow the addition of other elements when used in a claim. The phrase "consisting of" excludes additional elements, and the term "consisting essentially of" excludes material elements, but allows the inclusion of nonmaterial elements, such as labels, instructions for use, radio-opaque markers, stoppers, and the like.

BRIEF DESCRIPTION OF THE DRAWINGS

FIG. 1. Cross-section in the longitudinal axis of a prior art three layer balloon with groove, wherein upper layer is welded to middle layer that functions as a baffle at the groove. Because the upper layer is constrained by the weld, this balloon is conforming. Thus, the groove is retained even if the balloon is squeezed or overinflated. The prostate is cradled in the groove, and has much less tendency to slide off the balloon surface.

FIG. 2. Cross-section in the vertical axis of a unitary balloon showing a welded pinch and a weld to the lumen creating the groove.

FIG. 3. Cross-section in the vertical axis of a balloon made from two layers showing welded pinch and weld to lumen creating the groove.

DESCRIPTION OF EMBODIMENTS OF THE INVENTION

Figure 4:
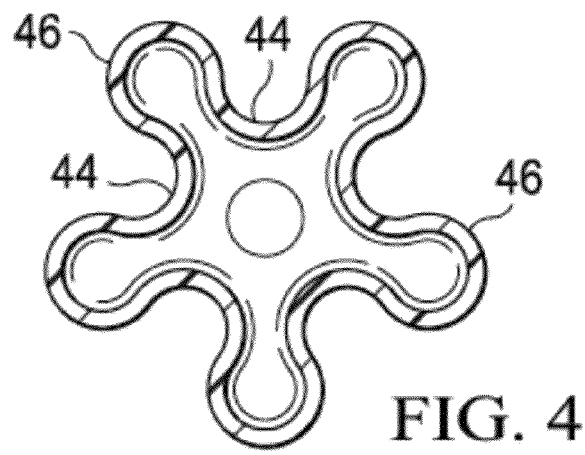
FIG. 4. Cross-section in the vertical axis of a fluted balloon mold. A fluted balloon produced with such mold would be easy to pinch weld to itself along one of the flutes, and the interior most end of a flute could also be welded to the lumen.

In both of the RadiaDyne inventions discussed above, the balloon was a single chambered balloon, albeit being made of three layers. Thus, the middle layer of balloon material had perforations or gaps so that the balloon consisted of a single fluid chamber and the entire device could be filled with a single lumen. This is shown in FIG. 1, which is a cross-section of the prior art rectal balloon 1 with lumen 2 having offset holes 3 for fluidic communication with the interior of the balloon. The use of a plurality of offset holes is generally preferred because it helps to prevent inadvertent hole blockage, e.g., by the balloon material or the rectal walls.

The prior art balloon comprised a top layer 4, a middle layer 5, and a bottom layer 6, which were welded together along the outer edges (not shown), and also affixed to the lumen, in this case at both the distal and proximal ends. The top layer 4 was welded 7 to the middle layer 5 along the central line of the balloon, but shifted proximally, so that the distal portion of the balloon bulged 8 more than the proximal portion on hyperinflation. The middle layer also had holes or gaps 9 so that the balloon comprised only a single fluid chamber and thus needed only a single fill means. The balloon filling means (typically a lumen, stopcock and luer connector) are not shown in this figure, but are typical in the art.

The weld 7 of top layer 4 to middle layer 5 provided a groove 10 (or indent or depression) having some depth into which the prostate could be wedged, and this grooved depression was retained on inflation and even on hyperinflation. The physical coupling of the middle baffle layer to the top layer provided a physical restraint against expansion or stretching, and the balloon was conforming—that is it held its shape even in the highly mobile environment of the rectum.

We now show how to make a similar conforming shaped balloon using a unitary or binary balloon construction and fewer welds.

A unitary balloon 27 is made by any conventional method and in any desired shape. For example, a tubular form is heated, immersed in a tank of coagulant solution for a few seconds, heated again and then immersed in a tank of latex. The coagulant causes the latex to coat the form, and the longer the forms are left in the tank, the thicker the coating that sticks to them. The forms must be inserted and removed at carefully controlled speeds to avoid trapping air bubbles and to achieve an even, thin coating.

The coated forms are then immersed in a tank of leaching solution (often plain water) to dissolve and leach away excess coagulant, and the rubber or polymer on the forms is dried and cured as needed. The balloons are then mechanically removed from the forms, e.g., with a spray of water or air.

A binary balloon is made by welding two films of the desired shape together at the edges.

The balloons are welded to make the desired conforming shape, as in FIG. 2. For example, a spot of glue is laid on the balloon's outer surface, and the balloon pinched at that spot to form a welded pinch 21. Alternatively, the pinch or fold 21 can be made first, and then welded or glued 25 to form the welded fold. This can be done with a jig that fits inside the balloon and folds it. In yet a third alternative, the pinch can be omitted, and the upper layer simply welded to a central lumen. In a fourth embodiment, both top and bottom layers can be welded to a lumen.

The lumen 29 is also coated with a spot of glue and inserted into the balloon, such that the pinch 21 is then welded 23 to the lumen. This can also be done with jigs to hold the balloon and lumen. The balloon is welded to at least the distal end of the lumen, preferably both ends, valve means are provided and if needed the balloon is sterilized before packaging. The position of the lumen and depth of groove can be influenced by changing the amount or depth of balloon pinch (-d-), a smaller pinch weld moving the lumen closer to the edge of the balloon and making the groove more shallow.

Although we describe a unitary balloon, it is also possible to make the shaped balloon in two layers as in FIG. 3. Although providing an additional weld along the outer edges of the two layers 33, 35, in some cases the two-layer construction may make the pinch/lumen welds easier, especially where the balloon is quite small and it is difficult to create a weld inside a unitary balloon. The balloon is as described above, but an additional weld 37 is shown at the outer edges of the two layers 33 and 35. The use of two layers also means that the two layers can be made of different materials, e.g., a less stretchy or thicker material on one side that will not stretch as much and thus provide a flatter surface. When the device is welded as in FIG. 3, it can be inverted so as to put the edge welds, which can be stiff or sharp, on the inside of the balloon if needed.

Figure 5A:
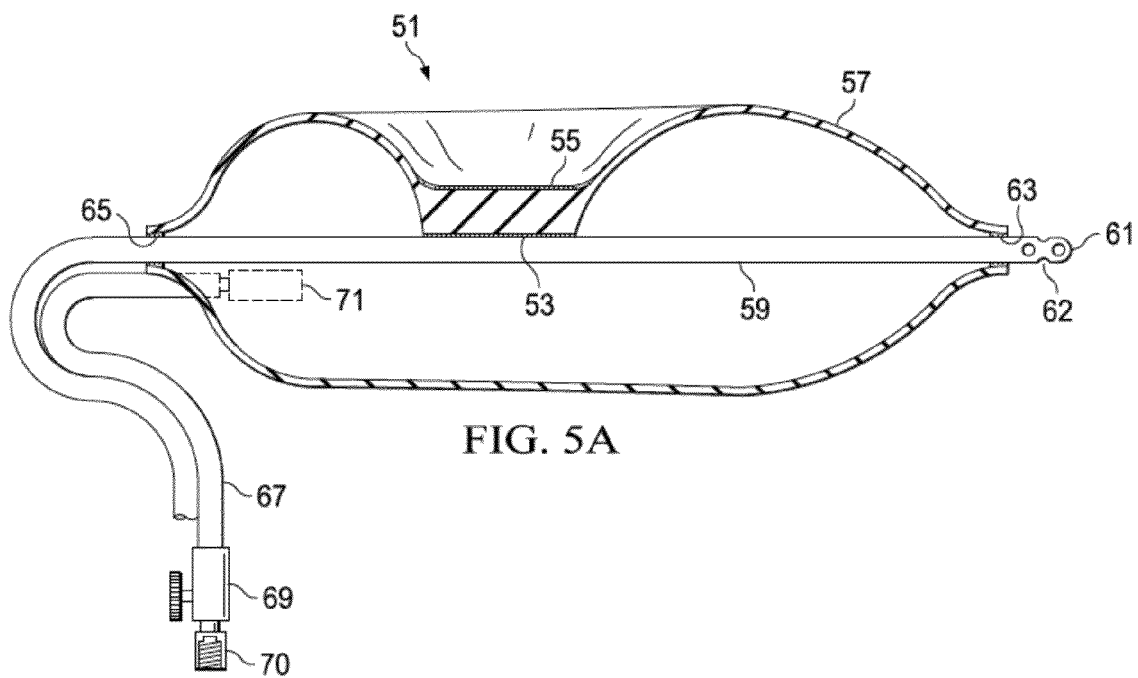
FIG. 5A. Cross-section in the longitudinal axis of a unitary balloon showing a welded pinch and a weld to the lumen creating the groove. This balloon is fitted with a gas lumen, and the fluid lumen does not traverse the entire length of the balloon.

A rectal balloon 57 is shown in cross section along its longitudinal axis in FIG. 5A. Here a gas lumen 59 traverses the balloon and is fitted with a soft rounded tip 61 having offset holes 62 for gas entry. The balloon is fitted at the proximal end with a low profile inlet fitment 71 and lumen 67 with valve means 69 and luer connector 70.

The pinch weld is shown at 55, and the weld to the lumen 53 is shown in black. Additional welds 63 and 65 are to the distal and proximal ends of gas lumen 59. The depression or groove 51 is thus clearly seen. On hyperinflation, the distal end of balloon 57 will bulge distally of the groove 51 (not shown) since there is more material here, and thus, there will be more stretch. Although not shown, such a rectal balloon is preferably fitted with numerical indicia for marking insertion depth, a lockable stopper for preventing changes in insertion depth, and radio-opaque markers.

Figure 5B:
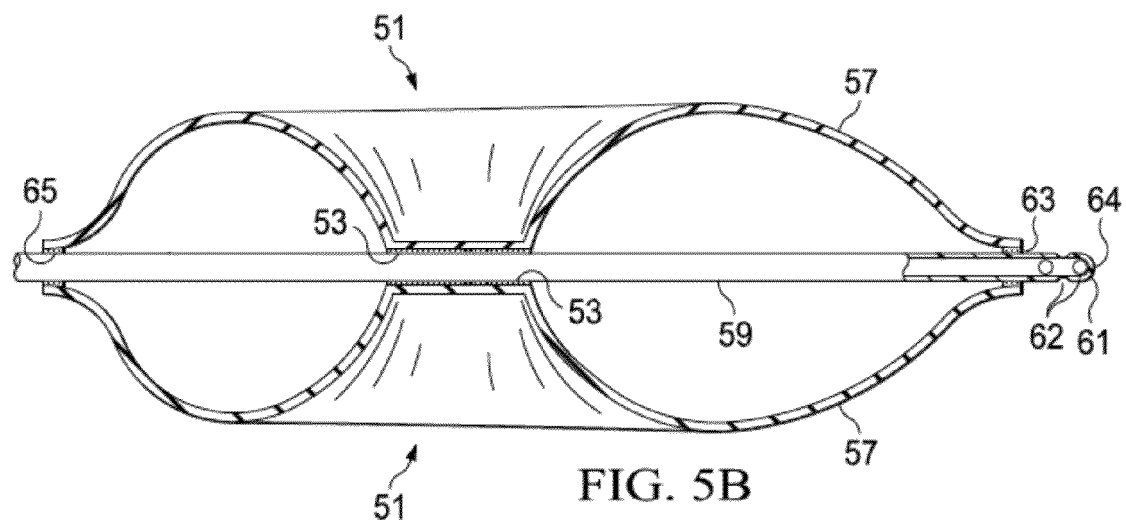
FIG. 5B. Cross-section in the longitudinal axis of a unitary balloon showing two welds to the lumen creating two grooves. This balloon is fitted with a gas lumen, and the fluid lumen does not traverse the entire length of the balloon.

FIG. 5B is a variation where the pinches are omitted entirely, and both layers are welded 53 to the lumen 59, creating a pair of deep grooves. Groove depth can be decreased on one or both sides by combining with a pinch weld, which allows the surface of the balloon to get farther away from the lumen.

Figure 5C:
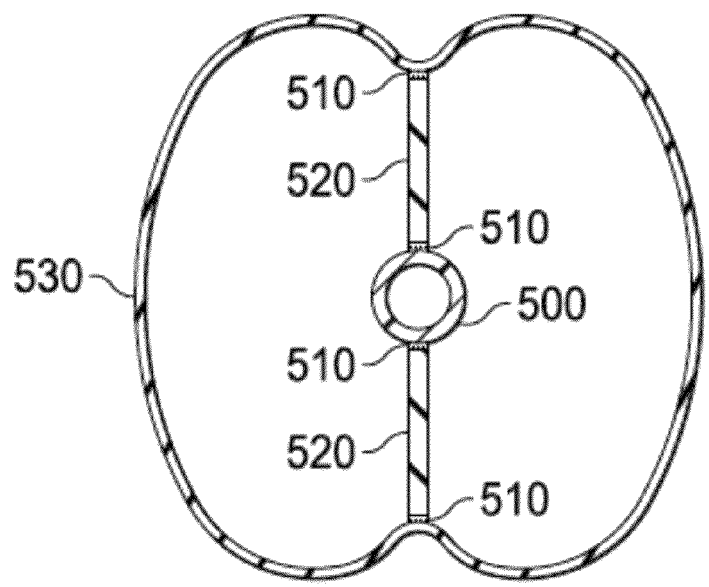
FIG. 5C. Cross-section in the vertical axis of a unitary balloon showing two baffles, each welded to the balloon and lumen.

In yet another variation, the pinch can be replaced with a baffle that is a small piece or strip of film welded at both the top layer and the lumen, wherein the width of the baffle controls the depth of the groove. FIG. 5C shows a variation, wherein there are two baffles 520 that are each welded 510 to the unitary balloon 530 and to the lumen 500. However, a single baffle can be used, and the baffle can attach to the lumen and balloon where a single depression is needed, or to both surface of the balloon where a pair of depressions is needed.

The rectal balloon is a simple tubular, ovoidal, or football shape herein, but it is also possible to make a fluted balloon as in FIG. 4, which can make the pinch and weld process easier. The flutes 46 also allow the balloon to be tightly vacuum folded against the lumen for insertion, and the creases 44 can be used to make a pinch weld.

Figure 6:
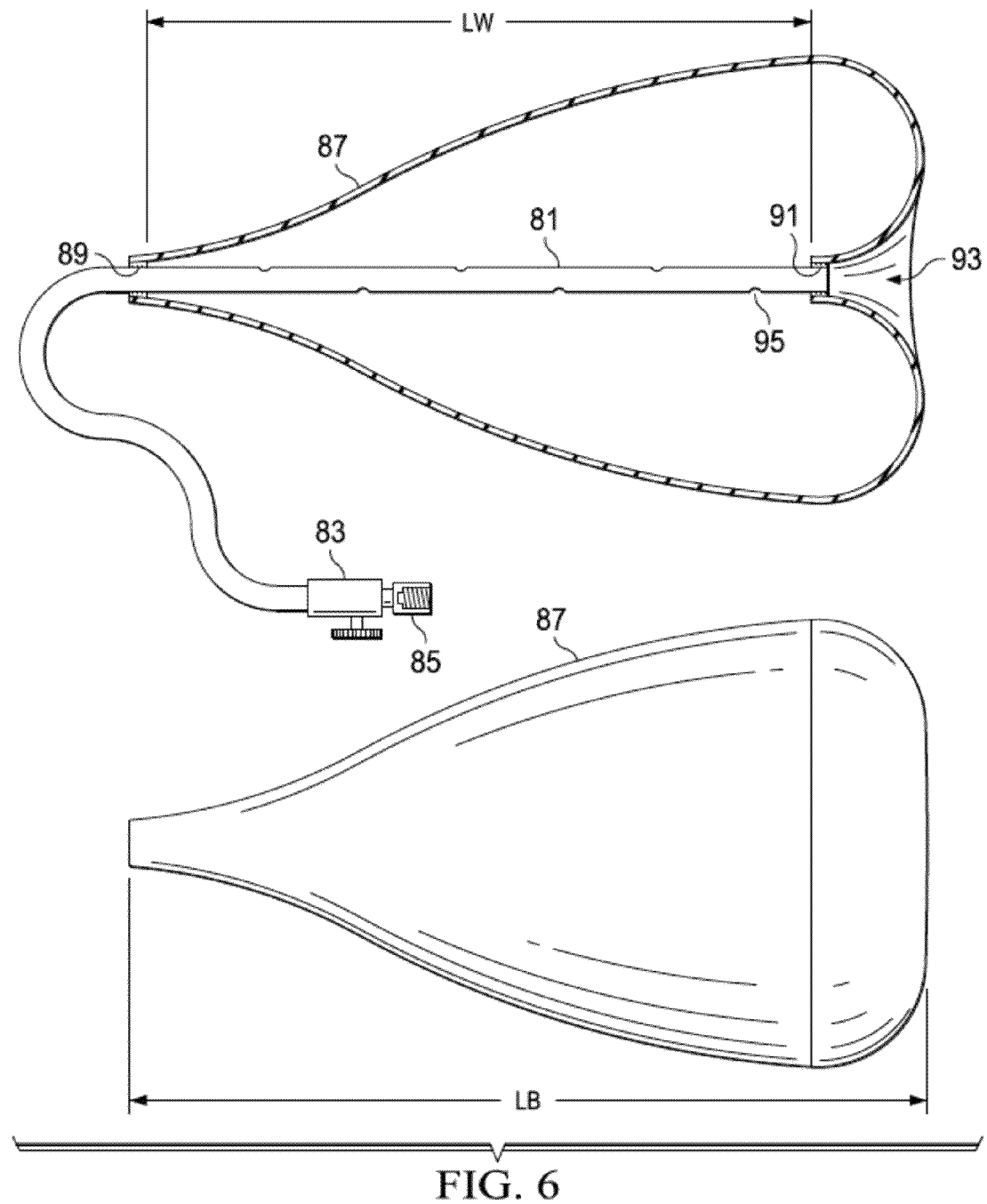
FIG. 6. Longitudinal view of vaginal balloon with distal weld creating distal cervical dimple.

In another embodiment shown in FIG. 6, the balloon 87 mold is shaped to reflect the vaginal vault, being substantially flared at the cervical (distal) end, and tapering at the proximal end. Such balloon can be welded at both proximal 89 and distal ends 91 of the lumen 81 having offset holes 95, but if the distance between welds on the lumen (LW) is shorter that the length of the balloon (LB), the inflated balloon will have a conforming distal dimple 93, into which the cervix can fit.

Using the pinch weld and lumen welds as described herein, it is possible to make a shaped balloon with one or more depressions anywhere on its surface. Further, bulges can be created with thinner or more elastic material, or shaped on a unitary balloon mold, or cut in a two layer balloon outline, as desired. Thus, using the principles described herein, a variety of conforming shapes are now possible.

If the depression does not need to be very deep, it is also possible to employ only pinch weld, and not weld the pinch to the lumen. Alternatively, a baffle can be used to decrease the depth of the depression.

If depressions on both sides are acceptable, the pinch can be omitted, and both upper and lower layers welded to a central lumen. Where shallower depressions are preferred, the two lumen weld version can also be combined with a pinch or a baffle, moving the bottom of the depression farther from the lumen. The length of the depressions will of course vary with the length of the weld, but for a prostate embodiment should preferably be ~1-5 cm, or about 3 cm.

Figure 7:
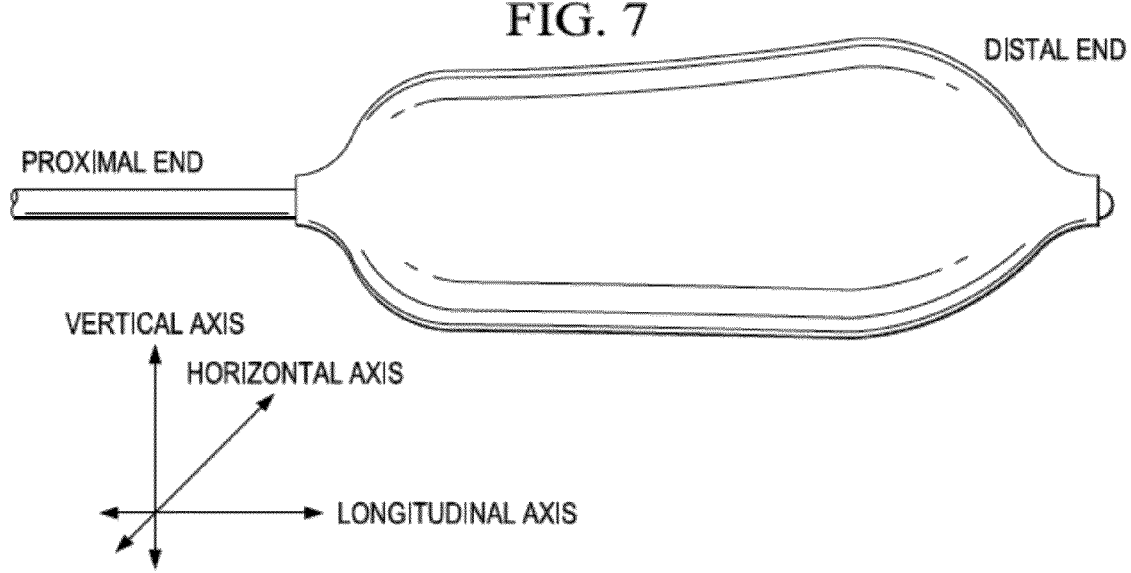
FIG. 7. Balloon axes as used herein.

The term distal as used herein is the end of the balloon inserted into the body cavity, while proximal is opposite thereto. The terms top and bottom are in reference to the figures only, and do not necessarily imply an orientation on usage. The length of balloon and lumen is the longitudinal axis, while a horizontal axis and vertical axis cross the longitudinal axis. See FIG. 7 showing these axes.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

What is claimed is:

1. A shaped medical balloon, comprising:
   a) a balloon;
   b) a lumen having a proximal end and a distal end; said lumen being in fluid communication with said balloon, said lumen being fitted with closable fluid entry means;
   c) said balloon having either: i) a unitary balloon construction or ii) a two layer balloon construction wherein edges of said two layers are welded together to form said balloon;
   d) said balloon having a central portion folded internally and welded together at said fold to make a welded pinch and said welded pinch is also welded to said lumen, thus creating a conforming depression in a surface of said balloon at said central portion,
   e) wherein said balloon is also welded to said lumen at a distal end and optionally at said proximal end.

2. The shaped medical balloon of claim 1, further comprising an opaque marker that can be imaged.

3. The shaped medical balloon of claim 1, further comprising a gas lumen that allows the passage of gas or fluid from the distal end to the proximal end.

4. The shaped medical balloon of claim 1, wherein said closable fluid entry means is i) a stopcock and luer connector, or ii) a luer lock.

5. The shaped medical balloon of claim 1, which is made of thermoplastic polyurethane.

6. The shaped medical balloon of claim 1, which is made of latex.

7. The shaped medical balloon of claim 1, which is made of silicone.

8. The shaped medical balloon of claim 1, which is translucent.

9. The shaped medical balloon of claim 1, which is made of translucent polymer having a 80-100 Shore A durometer, a tensile strength of at least 3000 psi; and 100% modulus of 500-1000 psi.

10. A method of radiation treatment comprising inserting the shaped medical balloon of claim 1 into a body cavity of patient, inflating said balloon, and providing radiation to said patient.

11. A method of radiation treatment comprising inserting the shaped medical balloon of claim 1 into a rectum of patient, inflating said balloon such that a prostate is immobilized in said conforming depression, and providing radiation to said prostate.

12. An improved prostate immobilization balloon wherein said balloon is fitted with closable lumen, the improvement comprising a central portion of said balloon pinched inside said balloon and welded together to itself and said central portion further welded to said lumen, thus creating a conforming depression in a surface of said balloon at said central portion.

13. An improved prostate immobilization balloon wherein said balloon is fitted with a central gas passing lumen traversing said balloon and having a rounded tip with fluid entry openings past a distal end of said balloon, said balloon also having a closable fluid entry means, the improvement comprising a portion of said balloon pinched inside said balloon and welded together and to itself and/or said lumen, thus creating a conforming depression in a surface of said balloon at said portion.

* * * * *